United States Patent [19]

De Carvalho

[11] Patent Number: 6,077,589

[45] Date of Patent: *Jun. 20, 2000

[54] ADHESIVE TAPE

[75] Inventor: Antonio Carlos Ribeiro De Carvalho, Taubate, Brazil

[73] Assignee: Johnson & Johnson Consumer Products, Inc., Skillman, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/126,977

[22] Filed: Jul. 31, 1998

Related U.S. Application Data

[63] Continuation of application No. 08/923,278, Sep. 4, 1997, abandoned, which is a continuation of application No. 08/691,221, Aug. 1, 1996, abandoned, which is a continuation of application No. 08/277,828, Jul. 20, 1994, abandoned.

[30] Foreign Application Priority Data

Jul. 27, 1993 [BR] Brazil ..................................... 9302518

[51] Int. Cl.[7] ................................. C09J 7/02; A61F 13/02
[52] U.S. Cl. .......................... 428/131; 428/174; 428/343; 604/307
[58] Field of Search .................................... 428/131, 156, 428/167, 174, 343; 604/307

[56] References Cited

U.S. PATENT DOCUMENTS

| | | | |
|---|---|---|---|
| 4,990,144 | 2/1991 | Blott | 604/304 |
| 5,167,613 | 12/1992 | Karami | 602/42 |
| 5,188,124 | 2/1993 | Feret | 128/889 |

*Primary Examiner*—Jenna Davis

[57] ABSTRACT

This invention refers to an adhesive tape, understood as an adhesive surface used, for example, to keep bandages in place on the skin or to effect immobilizations in traumatological cases, characterized by being provided with an apparent thickness. Such apparent thickness is made real by way of ondulations, projections or embossings, which ends are in contact with the skin surface, adhered thereto when in use.

3 Claims, 2 Drawing Sheets

ADHESIVE TAPE

This is a continuation of application Ser. No. 08/923,278, filed Sep. 4, 1997, now abandoned, which is a continuation of application Ser. No. 08/691,221, filed Aug. 1, 1996 now abandoned, which is a continuation of application Ser. No. 08/277,828, filed Jul. 20, 1994, now abandoned.

This invention refers to an adhesive tape, or an adhesive base substratum, used to make bandages or adhesive curatives.

In actual terms, the invention refers to adhesive curatives which allow one to avoid or minimize maceration of the healthy skin surrounding a wound.

In the following text, the term "adhesive tape" refers to any adhesive surface or material strap used to keep bandages in the due place, or to keep patients in certain positions over surgical tables, or to effect immobilizations in traumatological cases, etc. Yet in accordance with the foregoing, curative refers to a combination of an adhesive tape with a proper bandage to cover wounds, being generally a pad made of absorbent fibers.

Ready-for-use curatives, which are intended to protect portions of the body against physical and bacterial injuries, known in the state-of-the-art, comprise:

an adhesive tape (which is generally an adhesive substratum;

a pad in its central area, which has properties of absorbing exudates of the wound, and which does not adhere to the wound during the cicatrization process.

Such curatives firmly adhere to the healthy skin surrounding the wound by means of a pressure-sensitive adhesive. Using materials presenting moisture transmission rates lower than those of the skin in the manufacture of such curatives prevents natural sudoresis causing maceration in this region.

It is known that a healthy skin exposed to the environment keeps a certain rate of moisture transmission, in such a way that upon the existence of a barrier against said phenomenon, there is an unbalance of this dynamics. The skin begins to show maceration, herein understood as a softening, of ugly and apparently not healthy aspect, which is potentially more vulnerable to environment attacks, caused by moisture retention.

This invention aims at substantially eliminating or minimizing problems found in the prior technique in relation to maceration, by means of an adhesive tape which enables reduced skin occlusion in addition to an improved aeration provided by its tridimensional structure.

The invention also provides an adhesive tape which in fuction of its structure allows less adhesive/skin contact area.

It further provides an adhesive tape with features to weaken mechanic shocks against the skin, reducing the discomfort effect caused thereby.

This is an adhesive tape characterized for comprising a substratum with apparent thickness, which is made actual through projections, saliences and protuberances over the face of said adhesive tape, which ends are in contact with the body surface, adhered to the skin when in use.

There are state-of-the-art products which present substratum provided with apparent thickness, however turned solely to the protection of wounds, thus having functions and results which are totally different from those of the present invention.

North-American patent U.S. Pat. No. 4,990,144, by Smith & Nephew, refers to a non-adhesive curative provided with projections (either perforated or not) containing a medicinal product acting on the wound. The projections act as reservoirs which volume goes on the contrary direction of the patient's body, while the curative basis is a film which remains in substantial contact with the patient's skin, along its surface. That patent does not concern this invention, as it is intended to treat wounds, in addition to allowing an extensive and occlusive contact of an adhesive substratum over a non-wounded healthy skin.

German patent document DE2849176 refers to a bandage also intended to treat wounds. It is a bandage which central portion acts as a tunnel with perforated walls which remains over the wound, while the side wings of this tunnel are fixed in an occlusive manner to the skin surrounding the wound in order to keep said tunnel, either or not filled with medicine, over the wound. Also in that case the previous art is different from this invention because it is intended to protect and treat wounds, allowing occlusion over the healthy skin surrounding the wound.

American patent U.S. Pat. No. 4,543,750 describes a bandage intended to cover wounds, provided with two surfaces. The first one is ondulated and is in contact with the wound, and aims at having low adhesion to the same. The second surface, opposed to the first one, is flat and may optionally be adjacent to an absorbing material layer. There are preferably ports interconnecting the two surfaces of said bandage, in the regions with lower thickness, in order to allow the passage of exudates of the wound to the region outside the bandage. Also that patent does not refer to this invention, as it is intended to protect wounds.

This invention is intended to allow healthy skin surrounding a wound and over which the adhesive tape is applied, to remain as much as possible close to a normal status as far as exchange of moisture with the environment is concerned, avoiding or minimizing the maceration phenomenon. It is believed, without the invention depending on this statement, that the healthy skin near to a wound may have a positive influence over the cicatrization process thereof.

The invention is made actual through a flexible substratum provided with projections which are in contact with the skin only in their apexes or extreme points, leaving the remainder of this skin substratum distant, thus allowing free circulation of air and water vapour near to or around the non-adhered regions.

The mentioned projections may have any configurations and dimensions whatsoever, provided that they are adequate to the intended purpose, that is, to leave base substratum of the adhesive tape distant from the user's skin enabling space for air and/or water vapour circulation.

Following is a non-limitating list of possible realizations of projections of the adhesive tape of the present invention:

the substratum is ondulated and the ondulation apexes are adhered to the skin.

the substratum is flat, however provided with non-perforated embossings, and the embossing ends are adhered to the skin;

the substratum is flat, however provided with embossings which apexes are perforated, and the perforation edges are adhered to the skin;

the substratum is flat, however provided with embossings which sides are perforated, and the apexes of such embossings are adhered to the skin;

the substratum is flat, however provided with small stems or protuberances made of a different material from that of the substratum, as for example rubber, and the stem ends are adhered to the skin.

Embossing is herein understood as protuberances of a substratum, made of the same material thereof, and constrained to its thickness by mechanical means, as for example punction.

The following may be mentioned as examples of substratum:

polyethylene, polypropylene, vinyl chloride, polyurethane or any other polymeric plastic films;

microporous plastic, non-woven screen, or fabric, optionally covered by a waterproofing material layer;

laminates or compositions of the above materials.

The following drawings illustrate preferable realizations of this invention, without being limited to those cases, as many variations are possible within the scope of this invention as indicated in the attached claims.

DETAILED DESCRIPTION OF FIGURES

Figure 1:
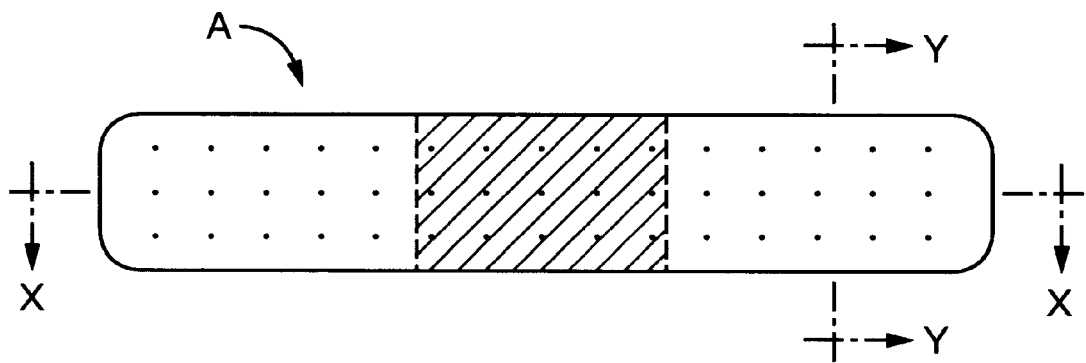
FIG. 1 schematically shows an upper view of a curative according to the invention.
Figure 2:
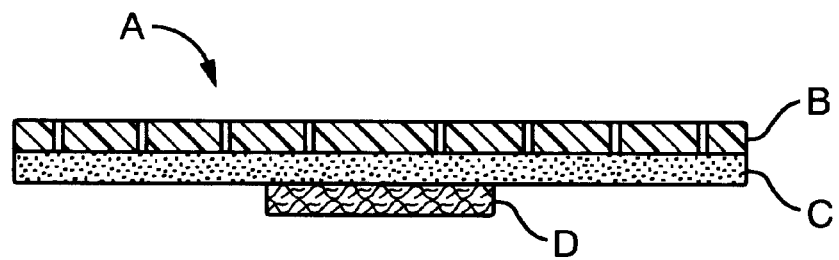
FIG. 2 schematically shows a longitudinal section of the curative of FIG. 1 along line XX.

FIGS. 1 and 2 show a possible realization of this invention, that is, a curative A for small skin cuts, provided with a perforated thin plastic film band B covered with an adhesive C and associated to a non-woven central pad D. Only the pad D is intended to cover and protect the wound, and the remainder of the plastic film is adhered to the healthy skin surrounding the wound.

Figure 3:
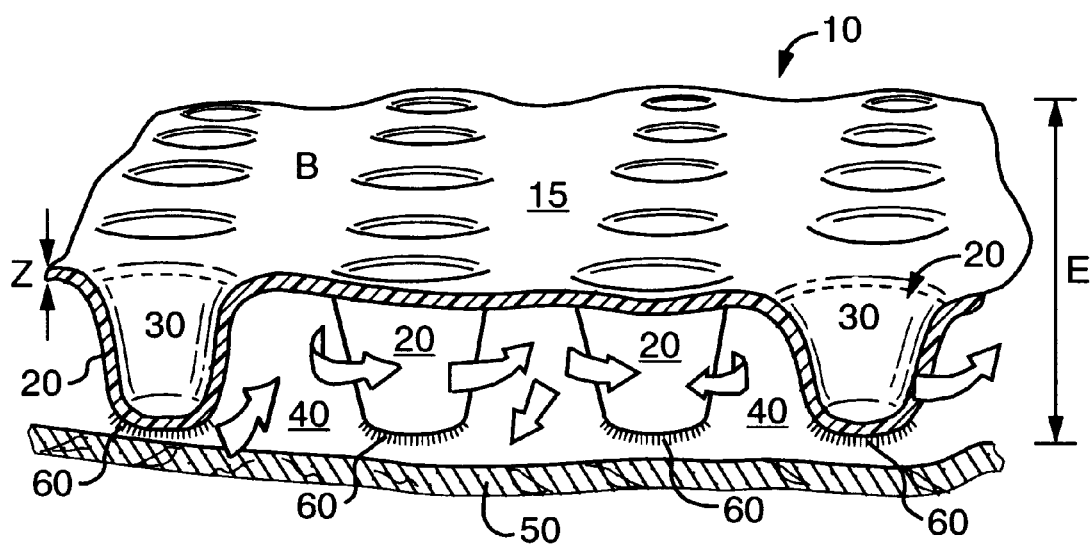
FIG. 3 schematically shows a cross section of the curative of FIG. 1 along line YY according to an alternative in which the adhesive basis of the curative is a plastic film with non-perforated embossings.

FIG. 3 shows a portion of the thin plastic film B in this specific realization indicated as 10, of actual average thickness Z, comprising a base 15 and embossings 20 which are similar to cone truncks, which provide an apparent thickness E between said base 15 and apexes 30 of the embossings 20.

There are realizations equivalent to that of this specific example wherein the film base is not necessarily flat, and wherein embossings may have any shape whatsoever, such as cylindric with circular basis, square or any other, or even without a determined geometric shape.

Embossed films and processes to obtain the same are known in the state-of-the-art. Patent documents U.S. Pat. No. 3,929,135, U.S. Pat. No. 4,342,314, U.S. Pat. No. 4,878,825 and EP0304617 may be mentioned as non-limiting examples.

Apexes 30 of embossings 20 are adhered to surface 40 of the user's skin 50 by means of an adhesive layer 60, which may be in a continuous or discontinuous form, involving in a larger or smaller extension the body of the embossings 20.

Proper adhesives to effect such adhesion are known in the state-of-the-art, as for example adhesives which are sensible to pressure, made of rubber or acrilic compound basis. Some examples of proper adhesives for this purpose are those mentioned in patent documents GB2070631, GB1280631 and EP35399. The application of such adhesives may be effected through a continuous layer, distributed along different points, or any other which may be adequate to the desired adhesion.

The contact of film 10 on the skin 50 allows air and water vapour circulation among embossings 20 (indicated by arrows) because of apparent thickness E between the surface 40 of the skin 50 and the film 10 base 15.

Figure 4:
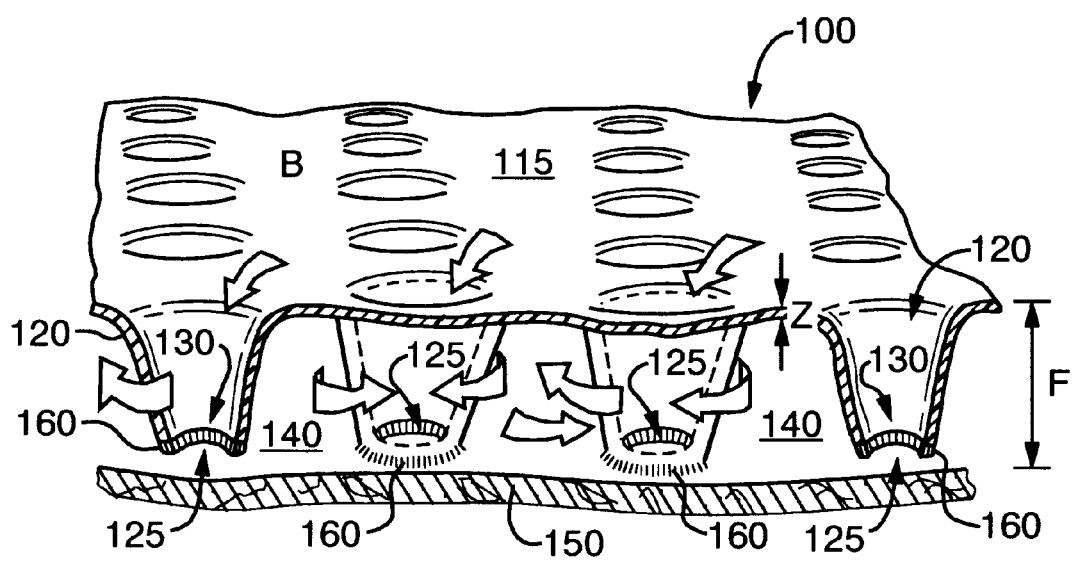
FIG. 4 schematically shows a cross section of the curative in FIG. 1 along line YY according to an alternative in which the adhesive basis of the curative is a plastic film with embossings provided with perforations in their apexes.

FIG. 4 shows another possible realization of this invention, that is, a thin plastic film B, herein indicated as 100, of actual thickness Z, comprising a base 115 and perforated embossings 120. Embossings 120 are provided with perforations 125 in the region of their apexes 130.

There are realizations which are equivalent to those of this specific example wherein the perforation of embossings 120 is not in the apexes 130 region, but rather on the sides of said embossings 120, eventually with more than one sole perforation per embossing.

The edges of the perforations 125 are adhered to the surface 140 of the user's skin 150, by means of an adhesive layer 160, which eventually covers the whole perforation 125 opening, depending on the conditions of the adhesive application process.

The contact of film 100 over skin 150 allows air and water vapour circulation (indicated by arrows) among perforated embossings 120 and internally within them, because of the apparent thickness F between skin 150 surface 140 and the film 100 base 115.

It can be easily observed in FIGS. 3 and 4 that the body of the embossings 20 and 120, in function of apparent thickness E and F serve as bumpers for mechanical shocks against base 10 or 100 of this invention curative thus enabling more comfort to the user thereof.

What is claimed is:

1. A bandage comprising an adhesive tape and a centrally located wound contacting pad, wherein said adhesive tape comprises a substratum and an adhesive, wherein said substratum comprises a surface having an apparent thickness, wherein said substratum further comprises a plurality of tapered embossings extending from said surface, wherein each of said embossings is defined by a side wall, a first opening in said surface and an apex positioned opposite said first opening, wherein the side wall extends between the first opening and the apex, wherein each said apex terminates at edges of a perforation, wherein said edges of each of said perforated apexes have adhesive applied thereto, and only said edges adhere to a user's skin during application of said bandage to the user's skin, and wherein said centrally located wound contacting pad is affixed to said adhesive and is adapted to be positioned adjacent to a wound of the user.

2. The curative of claim 1 wherein the substratum extends beyond said centrally located non-woven pad in two opposing directions.

3. The curative of claim 1 wherein the substratum extends beyond said centrally located non-woven pad in all directions.

* * * * *